United States Patent [19]

Bowden et al.

[11] 4,205,175

[45] May 27, 1980

[54] CHLORINATION PROCESS

[75] Inventors: Roy D. Bowden; Thomas Seaton, both of Runcorn, England

[73] Assignee: Imperial Chemical Industries Limited, London, England

[21] Appl. No.: 10,598

[22] Filed: Feb. 7, 1979

[30] Foreign Application Priority Data

Feb. 15, 1978 [GB] United Kingdom ............... 5982/78

[51] Int. Cl.² ........................................... C07D 213/26
[52] U.S. Cl. ................................................ 546/345
[58] Field of Search ......................................... 546/345

[56] References Cited

U.S. PATENT DOCUMENTS 3,186,994  6/1965  Johnston et al. .................... 546/345

OTHER PUBLICATIONS

Taplin, Chem. Abstracts, vol. 70, (No. 17), 77806v, Apr. 28, 1969.

Primary Examiner—Alan L. Rotman
Attorney, Agent, or Firm—Cushman, Darby & Cushman

[57] ABSTRACT

Partially-chlorinated derivatives of 3-methylpyridine, containing a single chlorine atom as substituent in the pyridine ring and either two or three chlorine atoms as substituents in the methyl group, are prepared by vapor-phase chlorination of 3-methylpyridine.

4 Claims, No Drawings

CHLORINATION PROCESS

This invention relates to a chlorination process, and more particularly to a process for the partial chlorination of 3-methylpyridine and to the products obtained thereby.

It is known that a variety of polychloropyridines may be obtained by the vapour phase chlorination of pyridine or substituted pyridines.

In the specification of U.K. Pat. No., 1,041,906 there is described a process for the manufacture of substituted pyridines containing one or more chlorine atoms as substituents in the pyridine ring which comprises interacting pyridine or a substituted pyridine with chlorine in the vapour phase at elevated temperature. The process described therein is especially applicable to the vapour-phase chlorination of pyridine itself, in which case high yields of pentachloropyridine are obtained. It is stated that with certain alkyl pyridines, for example 2-methyl pyridine, elimination of an alkyl substituent may occur during the chlorination process. An example of the chlorination of 2-methylpyridine at 500° C. shows the production of pentachloropyridine.

We have now found that when the starting material is 3-methylpyridine partial chlorination may be effected under certain conditions, to yield products containing a single chlorine atom as substituent in the pyridine ring and either two or three chlorine atoms as substituents in the methyl group.

According to the present invention there is provided a process for the preparation of one or more partially chlorinated derivatives of 3-methylpyridine, containing a single chlorine atom as substituent in the pyridine ring and either two or three chlorine atoms as substituents in the methyl group, which comprises chlorinating 3-methylpyridine in the vapour phase at a temperature in the range from 250° C. to 400° C., the proportion of chlorine employed being at least 5 moles per mole of 3-methylpyridine.

Among the partially-chlorinated derivatives which may be obtained by the process of the present invention are 2-chloro-5-(trichloromethyl)-pyridine and 2-chloro-5-(dichloromethyl)-pyridine. Other derivatives which may be obtained (depending upon the particular conditions used within the defined range) include 2-chloro-3-(trichloromethyl)-pyridine and 2-chloro-3-(dichloromethyl)-pyridine.

The compounds 2-chloro-3-(trichloromethyl)-pyridine, 2-chloro-5-(dichloromethyl)-pyridine and 2-chloro-3-(dichloromethyl)-pyridine are believed to be novel.

The chlorination process is preferably carried out at a temperature in the range from 300° C. to 400° C., for example in the range from 325° C. to 375° C.

The reactants are preferably diluted. The diluent may be inorganic, for example nitrogen and/or steam, or may be organic.

When an organic diluent is used, this is preferably a compound which is inert towards chlorine (for example carbon tetrachloride, which is the diluent especially preferred) or a compound such that any reaction with chlorine yields a product which is inert to further chlorination (for example chloroform, which may yield carbon tetrachloride).

When a gaseous diluent is used the 3-methylpyridine starting material may be vapourised in the stream of diluent vapour which serves as a carrier gas; when a liquid diluent is used, the starting material may be dissolved in the liquid diluent and the resulting solution may then be vaporised as a whole.

It is preferred to use at least 10 moles of chlorine per mole of 3-methylpyridine, for example from 10 to 20 moles of chlorine per mole of 3-methylpyridine.

When using a diluent which is reactive towards chlorine, for example chloroform, an appropriate additional amount of chlorine may be used to allow for that consumed by reaction with the diluent.

The reaction may be carried out in an unpacked reaction but for better control of the reaction temperature the reaction may be carried out in a fluidised bed of a material providing good heat transfer, for example a bed of microspheroidal silica.

Convenient residence times of the mixture in the reaction zone are, for example, between 10 and 30 seconds, but higher or lower residence times may be used if desired.

The partially-chlorinated derivatives produced may be recovered from the reaction products (and separated from one another if desired) by methods conventional in the art, for example fractional distillation and fractional crystallisation.

Partially-chlorinated derivatives of 3-methylpyridine are useful in the preparation of herbicidal compounds, for example in the preparation of alpha-4-(5-trifluoromethyl-2-pyridyloxy)-phenoxypropionic acid and its salts, esters, amides, and related compounds. These compounds are useful as herbicides for the control of weed grasses at rates of application from 0.025 to 5.0 kilograms per hectare.

Thus, for example the intermediates 2-chloro-5-(trifluoromethyl)-pyridine and 2-chloro-5-(difluoromethyl)-pyridine may be prepared by reacting 2-chloro-5-(trichloromethyl)-pyridine and 2-chloro-5-(dichloromethyl)-pyridine respectively with a fluorinating agent, for example antimony fluoride or liquid hydrogen fluoride.

The invention is illustrated by the following Examples:

EXAMPLE 1

A solution of 3-methylpyridine in carbon tetrachloride was fed to a packed vaporiser maintained at a temperature of 300° C. to 310° C. The issuing vapours were passed to a vertical glass tubular reactor of 3.8 inch bore held at a temperature of 350° C. where they were mixed with chlorine fed at a rate of 9.8 mole per hour (measured at 20° C.). The residence time was 20 seconds. The initial reaction mixture contained 16 moles of chlorine and 6 moles of carbon tetrachloride per mole of 3-methyl-pyridine.

The gaseous reactor effluent over a period of 1 hour was condensed and the resulting carbon tetrachloride solution was distilled to remove carbon tetrachloride. The residual solid was purified by recrystallisation from methylene chloride and the components were separated by preparative gas-liquid chromatography. The main products, identified by nuclear magnetic resonance spectra were 2-chloro-5-(trichloromethyl)-pyridine (38 grams, melting point 47° C.–49° C.) and 2-chloro-5-(dichloromethyl)-pyridine (52 grams, melting point 63° C.–64° C.

Other products identified were 2-chloro-3-(trichloromethyl)-pyridine and 2-chloro-3-(dichloromethyl)-pyridine, each of these two products comprising about 10 mole % of the total products separated.

EXAMPLE 2

The procedure was similar to that described in Example 1. The initial reaction mixture contained 16.7 moles of chlorine and 9.4 moles of carbon tetrachloride per mole of 3-methylpyridine. The flow rate of chlorine was 11.7 moles per hour and the residence time was 15 seconds. The reactor temperature was 340° C. The flow was continued for 1 hour.

The total weight of the separated products was 141 g and the composition was as follows:

| | |
|---|---|
| 2-chloro-5-(trichloromethyl)-pyridine | (45 mole %) |
| 2-chloro-3-(trichloromethyl)-pyridine | (10 mole %) |
| 2-chloro-3-(dichloromethyl)-pyridine | (45 mole %) |

EXAMPLE 3

A gaseous mixture containing 14.8 moles of chlorine, 6.0 moles of carbon tetrachloride and 11.7 moles of nitrogen per mole of 3-methylpyridine was passed through a fluidised bed of microspheroidal silica (AKZO 20) maintained at 290° C.

The flow rate of 3-methylpyridine was 2.7 liters per hour and the residence time was 10 seconds.

The products were analysed by gas-liquid chromatography and the main products were found to be 2-chloro-5-trichloromethylpyridine (21 mole %) and 2-chloro-3-dichloromethylpyridine (12 mole %).

EXAMPLE 4

The procedure was similar to that described in Example 3. The gaseous mixture contained 10.0 moles of chlorine, 6.0 moles of carbon tetrachloride and 18.4 moles of nitrogen per mole of 3-methylpyridine. The fluidised bed of microspheridal silica was maintained at 368° C. The flow rate of 3-methylpyridine was 2.5 liters per hour and the residence time was 10 seconds.

The main product was found to be 2-chloro-5-trichloromethylpyridine (33 mole %). The proportion of 2-chloro-3-dichloromethyl-pyridine was only 1 mole %.

What is claimed is:

1. A process for the preparation of a mixture of a partially chlorinated derivative of 3-methyl-pyridine selected from the group consisting of, 2-chloro-5-(trichloromethyl)-pyridine, 2-chloro-3-(trichloromethyl)-pyridine, 2-chloro-3-(dichloromethyl)-pyridine and 2-chloro-5-(dichloromethyl)-pyridine, which process comprises chlorinating 3-methyl-pyridine in the vapour phase at a temperature in the range from 250° C. to 400° C., the proportion of chlorine employed being at least 5 moles per mole of 3-methyl-pyridine.

2. A process according to claim 1 wherein the chlorination is carried out at a temperature in the range from 300° C. to 400° C.

3. A process according to claim 2 wherein the chlorination is carried out at a temperature in the range from 325° C. to 375° C.

4. A process according to claim 1 wherein the chlorination is carried out in the presence of a diluent from the group consisting of carbon tetrachloride and chloroform.

* * * * *